United States Patent [19]

Seki et al.

[11] Patent Number: 5,523,476

[45] Date of Patent: Jun. 4, 1996

[54] PROCESSES FOR PRODUCING TETRAFLUOROPHTHALIC ANHYDRIDE AND FLUOROBENZOIC ACIDS

[75] Inventors: Ryuji Seki; Koji Sugimoto; Seisaku Kumai, all of Yokohama, Japan

[73] Assignee: Asahi Glass Company Ltd., Tokyo, Japan

[21] Appl. No.: 391,060

[22] Filed: Feb. 21, 1995

[30] Foreign Application Priority Data

Feb. 23, 1994 [JP] Japan ..................... 6-25528
Feb. 24, 1994 [JP] Japan ..................... 6-26897
Mar. 4, 1994 [JP] Japan ..................... 6-34681

[51] Int. Cl.$^6$ ............... C07C 51/38; C07C 65/00; C07C 69/76; C07D 493/02
[52] U.S. Cl. ............... 562/479; 549/246; 560/53; 560/54; 560/83; 562/451; 562/456; 562/474; 562/480; 562/483; 562/493
[58] Field of Search ............... 549/246; 562/474, 562/451, 456, 493, 479, 480, 483; 560/83

[56] References Cited

U.S. PATENT DOCUMENTS 2,439,237  4/1948  Cass .
4,782,180  11/1988  Wemple et al. ............... 562/479
4,831,190  5/1989  Ataka et al. ............... 560/53
4,885,386  12/1989  Wemple et al. ............... 562/493
5,047,553  9/1991  Nowak et al. ............... 548/476
5,233,082  8/1993  Fertel et al. ............... 562/451
5,380,926  1/1995  Fertel et al. ............... 562/474

FOREIGN PATENT DOCUMENTS 0218111  4/1987  European Pat. Off. .

OTHER PUBLICATIONS

Patent Abstracts of Japan, vol. 13, No. 124 (C–580) (3472), Mar. 27, 1989, JP-A-63 295 529, Dec. 1, 1988.

Primary Examiner—Cecilia Tsang
Attorney, Agent, or Firm—Oblon, Spivak, McClelland, Maier & Neustadt

[57] ABSTRACT

A process for producing tetrafluorophthalic anhydride, which comprises chlorinating tetrachlorophthalic anhydride to obtain 3,3,4,5,6,7-hexachloro-1-[3H]-isobenzofuranone, then fluorinating it to obtain 3,4,5,6-tetrafluorophthaloyldifluoride and/or 3,3,4,5,6,7-hexafluoro-1-[3H]-isobenzofuranone, and further reacting the tetrafluorophthaloyldifluoride and/or the hexafluoro-1-[3H]-isobenzofuranone with an inorganic base or an organic acid to obtain tetrafluorophthalic anhydride.

8 Claims, No Drawings

PROCESSES FOR PRODUCING TETRAFLUOROPHTHALIC ANHYDRIDE AND FLUOROBENZOIC ACIDS

The present invention relates to novel processes for producing tetrafluorophthalic anhydride and fluorobenzoic acids which are useful as intermediates for medicines.

Tetrafluorophthalic anhydride is an important compound as an intermediate for medicines, agricultural chemicals and liquid crystals. Fluorobenzoic acids prepared from such tetrafluorophthalic anhydride, are important intermediates, from which various effects derived from fluorine atoms can be expected.

Methods for obtaining tetrafluorophthalic anhydride include (1) a method of dehydrating tetrafluorophthalic acid in the presence of an acid catalyst (Kogyo Kagaku Zasshi Vol. 73, 447, 1970), (2) a method of azeotropically dehydrating tetrafluorophthalic acid in xylene (Japanese Unexamined Patent Publication No. 306945/1990), and (3) a method of hydrolyzing tetrafluorophthalimide as the starting material in the presence of concentrated sulfuric acid, acetic acid and water, followed by removal of water (Japanese Examined Patent Publication No. 57255/1993). On the other hand, methods for producing fluorinated benzoic acids include (4) a method of synthesizing 2,3,4,5-tetrafluorobenzoic acid by heating tetrafluorophthalic acid in the presence of a tertiary amine for decarboxylation (Japanese Unexamined Patent Publication No. 13700/1989), (5) a method of synthesizing 2,3,4,5-tetralfluorobenzoic acid by heating tetrafluorophthalic acid in water in the presence of a metal oxide for decarboxylation (Japanese Unexamined Patent Publication No. 85349/1986), and (6) a method of producing 2,3,4,5-tetrafluorobenzoic acid by fluorinating 2,3,4,5-tetrachlorobenzonitrile (Japanese Unexamined Patent Publication No. 49263/1992).

Methods for obtaining 3-substituted-2,4,5-trifluorobenzoic acids include (7) a method of obtaining a 2,4,5-trifluoro-3-alkoxybenzoic acid from tetrafluorobenzonitrile in 8 steps (Japanese Unexamined Patent Publications No. 198664/1988 and No. 297366/1988), (8) a method of reacting a metal cyanide to a 2,3-dihalogeno-5,6-difluoroanisole to obtain a 2-halogeno-4,5-difluoro-3-methoxybenzonitrile, then adding water thereto to obtain a 2-halogeno-4,5-difluoro-3-methoxybenzamide, and further hydrolyzing it to obtain 2-halogeno-4,5-difluoro-3-methoxybenzoic acid (Japanese Unexamined Patent Publication No. 16746/1989), (9) a method of hydroxylating tetrafluorophthalic acid, followed by decarboxylation, alkylation and hydrolysis (Japanese Unexamined Patent Publication No. 268662/1989), and (10) a method of diesterifying tetrafluorophthalic acid followed by alkoxylation, hydrolysis and decarboxylation (Japanese Unexamined Patent Publication No. 279348/1991).

Methods (1) and (2) have a problem that it is difficult to prepare tetrafluorophthalic acid. Preparation of tetrafluorophthalic acid is disclosed in Japanese Unexamined Patent Publications No. 85349/1986, No. 61948/1987, No. 258442/1988 and U.S. Pat. No. 5,047,553). However, in each method, a large amount of a polar solvent is required in the purification step, and it is necessary to extract the product from an aqueous layer. Further, to obtain the desired product in a high purity, a further step of e.g. recrystallization is required. Thus, these methods are not industrially advantageous. Method (3) has a problem of treating waste liquid and a problem that yield is low. Methods (4) and (5) have a problem that tetrafluorophthalic acid used as the starting material is not readily available. Method (6) has problems that the yield in fluorination is low, and the solvent turns into tar. Method (7) requires many steps and thus is not industrially advantageous. Method (8) has a problem that the starting material is a compound which is not readily available. Method (9) has problems that the total yield of the overall process is low, it is necessary to carry out the decarboxylation step under a pressurized condition, a pressure reactor is required, and handling of dimethyl sulfate to be used for the alkylation, is difficult. Method (10) has problems that the starting materiel is hardly available, and the yield is low.

It is an object of the present invention to provide a novel process for producing tetrafluorophthalic anhydride and a process for producing tetrafluorobenzoic acids from the tetrafluorophthalic anhydride.

Namely, the present invention provides a process for producing tetrafluorophthalic anhydride, which comprises chlorinating tetrachlorophthalic anhydride to obtain 3,3,4,5,6,7-hexachloro-1-[3H]-isobenzofuranone, then fluorinating it to obtain 3,4,5,6-tetrafluorophthaloyldifluoride and/or 3,3,4,5,6,7-hexafluoro-1-[3H]-isobenzofuranone, and further reacting the tetrafluorophthalolyldifluoride and/or the hexafluoro-1-[3H]-isobenzofuranone with an inorganic base or an organic acid to obtain tetrafluorophthalic anhydride.

Further, the present invention provides processes for producing 2,3,4,5-tetrafluorobenzoic acid, a 2,3,4,5-tetrafluorobenzoic acid ester and a 3-substituted-2,4,5-trifluorobenzoic acid, from tetrafluorophthalic anhydride.

The route to produce tetrafluorobenzoic acid from tetrachlorophthalic anhydride is not necessarily clear, but may be represented by the following formula:

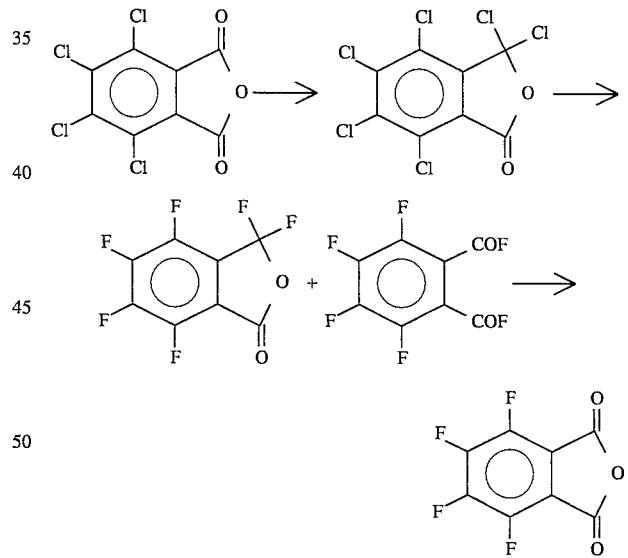

Tetrachlorophthalic anhydride is a compound which is readily available on an industrial scale. Conventional chlorination means and conditions can be used for the method of chlorinating the tetrachlorophthalic anhydride to obtain 3,3,4,5,6,7-hexachloro-1-[3H]-isobenzofuranone. For example, the method can be carried out by means of a usual chlorination agent. As the chlorination agent, phosphorus pentachloride, phosphorus oxychloride or thionyl chloride is preferred, and phosphorus pentachloride is particularly preferred. The chlorination agent is used usually in an amount of from 0.01 to 10 mols, preferably from 0.5 to 2 mols, per mol of tetrachlorophthalic anhydride.

The chlorination reaction can be carried out in the presence or absence of a solvent. The solvent is not particularly limited so long as it is capable of dissolving the reactants. However, an aprotic polar solvent or aprotic non-polar solvent is preferred. As the aprotic polar solvent, sulfolane, N,N-dimethyl formamide or 1,3-dimethylimidazolidinone may, for example, be mentioned. As the aprotic non-polar solvent, toluene, xylene, trichlorobenzene, dichlorobenzene or monochlorobenzene may preferably be employed. The solvent is used usually in an amount of from 0.01 to 100 parts by weight, preferably from 0.1 to 5 parts by weight, per part by weight of tetrachlorophthalic anhydride.

The reaction temperature for the chlorination reaction may suitably be changed depending upon the type of the chlorination agent, the presence or absence of a solvent, the type of the solvent or the amounts of the reactants. In a usual case, it is from 20° to 300° C., preferably from 100° to 200° C.

The 3,3,4,5,6,7-hexachloro-1-[3H]-isobenzofuranone obtained by the above chlorination reaction, is subjected to a fluorination reaction to obtain 3,4,5,6-tetraflouorophthaloyldifluoride and/or 3,3,4,5,6,7-hexafluoro-1-[3H]-isobenzofuranone.

The fluorination reaction can be carried out by reacting the isobenzofuranone with a fluorination agent. As the fluorination agent, an alkali metal fluoride is preferred. Particularly preferred is NaF, KF, RbF or CsF. Among them, KF is preferred, and particularly preferred is spray-dried potassium fluoride. The fluorination agent is used usually in amount of from 0.1 to 20 mols, preferably from 2 to 12 mols, per mol of 3,3,4,5,6,7-hexachloro-1-[3H]-isobenzofuranone. The above fluorination reaction can be carried out in the presence or absence of a solvent. However, it is preferred to conduct the reaction in the presence of a solvent. The solvent is not particularly limited so long as it is capable of dissolving the reactants. However, an aprotic solvent or an aprotic non-polar solvent is preferred. As the aprotic solvent, N,N-dimethylformamide, N,N-dimethylacetamide, dimethylsulfoxide, dimethylsulfone, sulfolane, hexamethylphosphorietriamide, N-methyl-2-pyrrolidone, 1,3-dimethylimidazolidinone, acetonitrile, benzonitrile, dioxane, diglyme or tetraglyme is, for example, preferred, and sulfolane or N,N-dimethylformamide is particularly preferred. As the aprotic non-polar solvent, toluene, xylene, trichlorobenzene, dichlorobenzene or monochlorobenzene is, for example, preferred. The solvent is used usually in an amount of from 0.5 to 10 parts by weight, preferably from 1 to 5 parts by weight, per part by weight of the 3,3,4,5,6,7-hexachloro-1-[3H]-isobenzofuranone.

At the time of the fluorination reaction, a phase transfer catalyst may be incorporated as a reaction accelerator. As the phase transfer catalyst, a quaternary ammonium salt such as tetramethylammonium chloride or tetrabutylammonium bromide, a pyridinium salt such as N-neopentyl-4-(N',N'-dimethylamino-pyridinium chloride or N-(2-ethyl-hexyl)-4-(N',N'-dimethylamino)pyridinium chloride, or a quaternary phosphonium salt such as tetrabutylphosphonium bromide or tetraphenylphosphonium bromide, may, for example, be mentioned. Among them, tetrabutylphosphonium bromide or tetraphenylphosphonium bromide is preferred. The phase transfer catalyst is used usually in an amount of from 1 to 50 parts by weight, preferably from 5 to 20 pars by weight, per 100 parts by weight of the 3,3,4,5,6,7-hexachloro-1-[3H]-isobenzofuranone. The reaction temperature for the above fluorination reaction is usually from 50° to 250° C., preferably from 100° to 230° C.

3,4,5,6-Tetrafluorophthaloyldifluoride and 3,3,4,5,6,7-hexafluro-1-[3H]-isobenzofuranone obtained by the above fluorination reaction, are usually obtained in the form of a mixture. However, they may be separated, as the case requires, to obtain them individually alone.

The 3,4,5,6-tetrafluorophthaloyldifluoride and/or the 3,3,4,5,6,7-hexafluoro-1-[3H]-isobenzofuranone obtained by the above method, is reacted with an inorganic base or an organic acid to form tetrafluorophthalic anhydride.

The proportions of the 3,4,5,6-tetrafluorophthaloyldifluoride and the 3,3,4,5,6,7-hexafluoro-1-[3H]-isobenzofuranone are not particularly limited. They may be used in any proportions, or they may be used individually alone.

As the inorganic base, an alkali metal salt is preferred. As the alkali metal salt, sodium hydrogen carbonate, potassium hydrogen carbonate, sodium carbonate, potassium carbonate, sodium hydroxide, potassium hydroxide or calcium carbonate is, for example, preferred. Particularly preferred is sodium carbonate or potassium carbonate. The inorganic base is used usually in an amount of from 0.01 to 50 parts by weight, preferably from 0.3 to 1.5 parts by weight, per part by weight of the total amount of the 3,4,5,6-tetrafluorophthalolydifluoride and the 3,3,4,5,6,7-hexafluoro-1-[3H]-isobenzofuranone.

As the organic acid, an organic carboxylic acid is preferred, which may be an aliphatic carboxylic acid or an aromatic carboxylic acid. As the aliphatic carboxylic acid, formic acid, acetic acid, propionic acid, butanoic acid or trifluoroacetic acid is, for example, preferred. As the aromatic carboxylic acid, benzoic acid, p-chlorobenzoic acid, 2,3-dichlorobenzoic acid or p-methyl benzoic acid is, for example, preferred. Among them, an aliphatic carboxylic acid is preferred, and acetic acid is particularly preferred. The organic carboxylic acid is used usually in an amount of from 0.01 to 1000 mols, preferably from 0.5 to 20 mols, per mol of the total amount of the 3,4,5,6-tetrafluorophthaloyldifluoride and the 3,3,4,5,6,7-hexafluoro-1-[3H]-isobenzofuranone.

The above mentioned reaction of the 3,4,5,6tetrafluorophthaloyldifluoride and/or 3,3,4,5,6,7-hexafluoro-1-[3H]-isobenzofuranone with the inorganic base or the organic acid, can be carried out by heating in the presence or absence of a solvent.

As the solvent, an aprotic solvent is preferred. As the aprotic solvent, an aprotic non-polar solvent or an aprotic polar solvent may be used. As the aprotic polar solvent, N,N-dimethylformamide, N,N-dimethylacetamide, dimethylsulfoxide, dimethylsulfone, sulfolane, hexamethylphosphoric triamide, N-methyl-2-pyrrolidone, 1,3-dimethylimidazolidinone, acetonitrile, benzonitrile, dioxane, diglyme or tetraglyme is, for example, preferred. As the aprotic non-polar solvent, toluene, xylene, naphthalene, chlorobenzene or dichlorobenzene is, for example, preferred.

The amount of the solvent for the reaction with the inorganic base is usually from 0.01 to 10 parts by weight, preferably from 0.5 to 5 parts by weight, per part by weight of the total amount of the 3,4,5,6-tetrafluorophthaloyldifluoride and the 3,3,4,5,6,7-hexaflouro-1-[3H]-isobenzofuranone. Further, the amount of the solvent for the reaction with the organic acid is usually from 0.01 to 100 parts by weight, preferably from 0.5 to 20 parts by weight, per part by weight of the total amount of the 3,4,5,6-tetrafluorophthaloyldifhloride and the 3,3,4,5,6,7-hexafluoro-1-[3H]-isobenzofuranone.

The reaction temperature is usually at a level of from 300° to 400° C. in either case of the reaction with the inorganic base or the reaction with the organic acid. However, the temperature may suitably be changed depending upon the type or amount of the inorganic base or the organic acid, the presence or absence, or the type of the solvent, or the amount of the reactant.

From the obtained tetrafluorophthalic anhydride, a 2,3, 4,5,-tetrafluorobenzoic acid ester, 2,3,4,5-tetraflurorobenzoic acid and a 3-substituted-2,4,5-trifluorobenzoic acid can be synthesized, which are useful as intermediates for medicines and agricultural chemicals.

Namely, tetrafluorophthalic anhydride is reacted with a hydroxyl compound to obtain a 3,4,5,6-tetrafluorophthalic acid-monoester, and then it is decarboxylated to obtain a 2,3,4,5-tetrafluorobenzoic acid ester. Further, the 2,3,4,5-tetrafluorobenzoic acid ester is hydrolyzed to obtain 2,3,4, 5-tetrafluorobenzoic acid. The route for producing the 2,3, 4,5-tetraflouorobenzoic acid ester and the 2,3,4,5-tetraflouorobenzoic acid, from tetrafluorophthalic anhydride, is not necessarily clear, but may be represented by the following formulas.

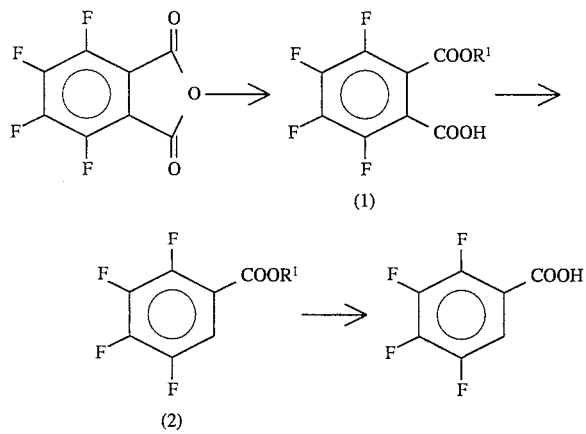

In the above formulas, $R^1$ is a monovalent group having a hydroxyl group —OH removed from the hydroxyl compound R'OH.

In the following description, the "alkyl group" may be of a straight chain structure, a branched structure or a ring structure partly or in its entirety. The carbon number of the alkyl group is preferably from 1 to 10, more preferably from 1 to 6. Preferred specific examples of the alkyl group include a methyl group, an ethyl group, a propyl group, an isopropyl group, an isobutyl group, a t-butyl group, a pentyl group and a hexyl group.

The "fluoroalkyl group" means a group of a structure having part or all of hydrogen atoms of the above "alkyl group" substituted by fluorine atoms. The fluoroalkyl group is preferably a perfluoroalkyl group of a structure having all of hydrogen atoms of the "alkyl group" substituted by the fluorine atoms, or the one wherein such a perfluoroalkyl group is present at the terminal portion of the fluoroalkyl group. For example, it may be a 2,2,2-trifluoroethyl group or a 3,3,3-trifluoropropyl group.

The "aryl group" is a monovalent aromatic hydrocarbon group, which may have a substituent (such as a lower alkyl group, a halogen atom, a lower alkoxy group, or a lower alkylamino group). As the aryl group, a phenyl group or its derivative is preferred. For example, a phenyl group, a tolyl group, a p-halophenyl group (such as a p-chlorophenyl group or p-bromophenyl group) or an alkoxy phenyl group (such as a methoxy phenyl group or an ethoxy phenyl group) may, for example, be mentioned.

Firstly, tetrafluorophthalic anhydride is reacted with a hydroxyl compound to obtain a 3,4,5,6-tetrafluorophthalic acid-monoester.

The hydroxyl compound is not particularly limited, but an alcohol or a hydroxyl aryl compound is preferred. As the alcohol, an alcohol having one hydroxyl group is preferred. As the alcohol having one hydroxyl group, an alkyl alcohol or a fluoroalkyl alcohol is preferred. Further, as the hydroxyl aryl compound, a compound having an aryl group and one hydroxyl group bonded to each other, is preferred.

As the alkyl alcohol, an alcohol having a $C_{1-10}$ alkyl group, preferably a $C_{1-6}$ alkyl group, is preferred, and it may be a primary alcohol, a secondary alcohol or a tertiary alcohol. The primary alcohol may, for example, be methanol or ethanol, the secondary hydroxyl compound may, for example, be isopropanol or 2-butanol, and the tertiary hydroxyl compound may, for example, be t-butanol or 2-methyl-2-butanol.

As the fluoroalkyl alcohol, trifluoroethanol or 3,3,3-trifluoropropanol is preferred, since it is readily available.

As the hydroxyl aryl compound, phenol or an alkoxy phenol is preferred. Phenol, p-methoxy phenol or p-ethoxy phenol is particularly preferred.

The reaction of the tetrafluorophthalic anhydride with the hydroxyl compound is preferably carried out in the presence of an acid catalyst or a base catalyst.

As the acid catalyst, an inorganic acid such as hydrochloric acid, phosphoric acid or sulfuric acid, or an organic acid such as p-toluene sulfonic acid, acetic acid or trifluoroacetic acid, is preferred. As the base catalyst, an inorganic base such as sodiumhydrogen carbonate, potassiumhydrogen carbonate, sodium carbonate, potassium carbonate, sodium hydroxide or potassium hydroxide, or an organic base such as triethylamine, tri-n-butylamine or tri-n-octylamine, is preferred. The acid catalyst or the base catalyst is used usually in an amount of from 0.001 to 100 mols, preferably from 0.01 to 2 mols, per mol of the tetrafluorophthalic anhydride.

The temperature for the reaction of the tetrafluorophthalic anhydride with the hydroxyl compound, may suitably be changed depending upon the reactants and the presence or absence, the amount or the type of the acid or base catalyst. In a usual case, it is preferably about the refluxing temperature of the hydroxyl compound, and it is usually within a range of from 0° to 220° C.

By the reaction of the tetrafluorophthalic anhydride with the hydroxyl compound, a 3,4,5,6-tetrafluorophthalic acid-monoester represented by the formula (1) is formed. In the formula (1), $R^1$ is a monovalent group having a hydroxyl group removed from the hydroxyl compound, and it is preferably an alkyl group, an aryl group or a fluoroalkyl group.

The 3,4,5,6-tetrafluorophthalic acid-monoester (1) is subjected to a decarboxylation reaction to obtain a 2,3,4,5-tetrafluorobenzoic acid ester. The 2,3,4,5-tetrafluorobenzoic acid ester is a compound represented by the above formula (2).

The decarboxylation reaction can be carried out in the presence or absence of a solvent, preferably in the presence of a solvent, under heating. As the solvent, water, a protic organic solvent (e.g. a glycol such as ethylene glycol), an aprotic polar organic solvent (e.g. dimethyl acetamide or sulfolane), or an aprotic non-polar organic solvent (e.g. toluene or xylene) is preferred.

Further, a catalyst may be present in the decarboxylation reaction. As the catalyst, a tertiary amine such as triethylamine, tri-n-butylamine or tri-n-octylamine, or a hydroxide, a fluoride, a carbonate, a hydrogen carbonate, a sulfate or an organic salt of ammonia, an alkali metal or an alkaline earth metal, may, for example, be used. Otherwise, it may be an acid catalyst such as sulfuric acid, hydrochloric acid or p-toluene sulfonic acid. The catalyst is used usually in a amount of from 0.01 to 10 mols, preferably from 0.1 to 5 mols, per mol of the 2,3,4,5-tetrafluorobenzoic acid ester (2).

When the solvent is used, its amount is usually within a range of from 0.01 to 1,000 parts by weight, preferably from 0,.1 to 100 parts by weight, per 100 parts by weight of the 3,4,5,6-tetrafluorophthalic acid-monoester (1). Further, the reaction temperature is usually from 100° to 220° C., and the reaction time is usually from 0.5 to 20 hours.

The 2,3,4,5-tetrafluorobenzoic acid ester (2) formed by the above reaction, is hydrolyzed to obtain 2,3,4,5-tetrafluorobenzoic acid.

The hydrolysis can be carried out by a conventional or well known method. In a usual case, the reaction is preferably conducted in the presence of water in an acidic or basic condition. The amount of water is not particularly limited. However, in a usual case, it is preferably from 1 to 10 parts by weight per part by weight of the 2,3,4,5-tetrafluorobenzoic acid ester (2). As the acid, hydrochloric acid, phosphoric acid or sulfuric acid is, for example, preferred. As the base, sodiumhydrogen carbonate, potassiumhydrogen carbonate, sodium carbonate, potassium carbonate, sodium carbonate or potassium hydroxide is, for example, preferred. The amount of the acid or the base is usually from 0.01 to 10 parts by weight, preferably from 0.1 to 5 parts by weight, per part by weight of the 2,3,4,5-tetrafluorobenzoic acid ester (2).

The reaction temperature for the hydrolysis reaction is preferably from 30° to 220° C., but it may be changed depending upon the type and concentration of the acid or the base. Further, the above mentioned respective reactions for monoesterification, decarboxylation and hydrolysis may be conducted in a single step.

Further, from tetrafluorophthalic anhydride, it is also possible to synthesize a 3-substituted-2,4,5trifluorobenzoic acid useful as an intermediate for medicines and agricultural chemicals.

Namely, tetrafluorophthalic anhydride and a hydroxyl compound are reacted to obtain a 3,4,5,6-tetrafluorophthalic acid-monoester, then, the fluorine atom at the p-position to the ester group of the 3,4,5,6-tetrafluorophthalic acid-monoester is substituted by a $R^3O$ group (wherein $R^3$ is a monovalent organic group) to obtain a 4-substituted-3,5,6-trifluorophtahlic acid-1-ester, then it is hydrolyzed to obtain a 4-substituted-3,5,6-trifluorophthalic acid, and it is further decarboxylated to obtain a 3-substituted-2,4,5-trifluorobenzoic acid.

The route for synthesizing the 3-substituted-2,4,5-trifluorobenzoic acid from the tetrafluorophthalic anhydride is not necessarily clear, but it may be represented by the following formulas.

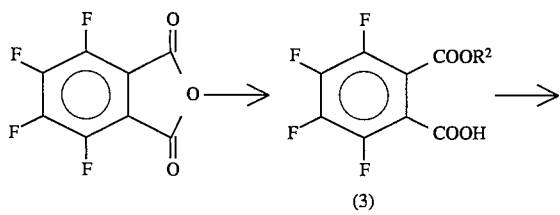

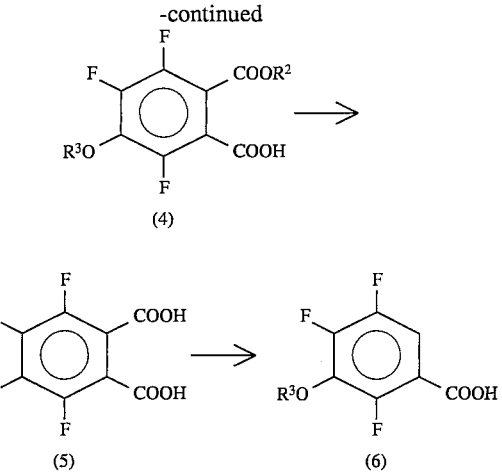

In the above formulas, $R^3$ is a monovalent group having a hydroxyl group removed from the hydroxyl compound, and $R^3$ is a monovalent organic group.

Tetrafluorophthalic anhydride is reacted with a hydroxyl compound to obtain a 3,4,5,6-tetrafluorophthalic acid-monoester. The 3,4,5,6-tetrafluorophtalic acid-monoester is a compound of the formula (3), which is the same as the compound of the above formula (1). $R^3$ is preferably an alkyl group, an aryl group or a fluoroalkyl group of the same type as $R^1$. This reaction can be conducted in the same manner as the above mentioned reaction for synthesizing the compound of the formula (1) from tetrafluorophthalic acid.

The above 3,4,5,6-tetrafluorophthalic acid-monoester (3) is converted to a 4-substituted-3,5,6-trifluorophthalic acid-1-ester by substituting the fluorine atom at the p-position to the ester group, i.e. the fluorine atom at the 4-position, by a $R^3O$ group (wherein $R^3$ is a monovalent organic group). The 4-substituted-3,5,6-trifluorophthalic acid-1-ester is a compound of the above formula (4). In the formula (4), $R^3$ is a monovalent organic group, which is preferably an alkyl group, a fluoroalkyl group or an aryl group.

The reaction for substituting the fluorine atom at the 4-position of the 3,4,5,6-tetrafluorophthalic acid-monoester (3), can be conducted in the presence of a metal alkoxide or a hydroxyl compound and an inorganic base.

As the metal alkoxide, an alkali metal alkoxide or an alkaline earth metal alkoxide is preferred. Particularly preferred is an alkali metal alkoxide. As the alkali metal alkoxide, sodium methoxide or potassium methoxide is preferred. The metal alkoxide is used usually in an amount of from 0.01 to 10 mols, preferably from 0.5 to 3 mols, per mol of the 3,4,5,6-tetrafluorophthalic acid-monoester.

The reaction of the 3,4,5,6-tetrafluorophthalic acid-monoester (3) and the metal alkoxide, can be conducted in the presence or absence of a solvent. However, it is preferred to carry out the reaction in the presence of a solvent. As the solvent, water, a protic organic solvent or an aprotic organic solvent is preferred. Particularly preferred is a protic organic solvent. As the protic organic solvent, an alcohol or a glycol is preferred, and particularly preferred is methanol, ethanol or ethylene glycol. As the aprotic organic solvent, an aprotic polar solvent such as dimethyl acetamide or sulfolane, or an aprotic non-polar solvent such as toluene or xylene is preferred. The solvent is used usually in an amount of from 0.01 to 1,000 parts by weight, preferably from 0.5 to 100 parts by weight, per 100 parts by weight of the 3,4,5,6-tetrafluorophthalic acid-monoester.

In the reaction of the 3,4,5,6-tetraluorophthalic acid-monoester (3) with the hydroxyl compound and the inorganic base, as the hydroxyl compound, the same alcohol or hydroxyl aryl compound as mentioned above is preferred. As the inorganic base, a metal hydroxide or metal carbonate may be employed, and a metal hydroxide is preferred. As the metal hydroxide, an alkali metal hydroxide or an alkaline earth metal hydroxide is preferred, and particularly preferred is an alkali metal hydroxide. As the alkali metal hydroxide, lithium hydroxide, sodium hydroxide or potassium hydroxide is preferred, and particularly preferred is sodium hydroxide or potassium hydroxide. As the metal carbonate, an alkali metal carbonate or an alkaline earth metal carbonate is preferred, and particularly preferred is an alkali metal carbonate. As the alkali metal carbonate, sodium carbonate, potassium carbonate, sodiumhydrogen carbonate or potassiumhydrogen carbonate is preferred.

The hydroxyl compound is used usually in an amount of from 0.1 to 1,000 mols, preferably from 0.5 to 100 mols, per mol of the 3,4,5,6-tetrafluorophthalic acid-monoester (3). Further, the inorganic base is used usually in an amount of from 0.01 to 10 mols, preferably from 0.5 to 3 mols, per mol of the 3,4,5,6-tetrafluorophthalic acid-monoester.

The reaction temperature for the reaction of the 3,4,5,6-tetrafluorophthalic acid-1-ester (3) with the metal alkoxide, or the hydroxyl compound and the inorganic base, is usually from 0° to 300° C., preferably from 10° to 100° C., and the reaction time is usually from 0.1 to 100 hours, preferably from 0.5 to 10 hours.

The above 4-substituted-3,5,6-trifluorophthalic acid-1-ester (4) is hydrolyzed to a 4-substituted-3,5,6trifluorophthalic acid. The 4-substituted-3,5,6-trifluorophthalic acid is a compound of the formula (5).

The hydrolysis reaction can be conducted in accordance with conventional or well known conditions. The hydrolysis reaction can be carried out in the same manner and conditions as the above mentioned hydrolysis reaction of the 2,3,4,5-tetrafluorobenzoic acid ester (2) to obtain the 2,3,4,5-tetrafluorobenzoic acid.

The above 4-substituted-3,5,6-trifluorophthalic acid (5) is converted to a 3-substituted 2,4,5-trifluorobenzoic acid by subjecting the carboxyl group at the p-position of the $R^3O$-group i.e. at the 1-position, to a decarboxylation reaction. The 3-substituted-2,4,5-trifluorobenzoic acid is a compound of the formula (6).

The reaction for decarboxylating the carboxyl group at the 1-position can be carried out in accordance with a conventional or well know decarboxylation reaction method. The decarboxylation reaction is preferably conducted in the same manner and conditions as in the above mentioned decarboxylation reaction of the 3,4,5,6-tetrafluorophthalic acid-monoester (1) to obtain the 2,3,4,5-tetrafluorobenzoic acid ester (2). The decarboxylation reaction can be conducted in the presence or absence of a solvent, preferably in the presence of a solvent, under heating. Further, also in the decarboxylation reaction of the 4-substituted-3,5,6-trifluorophthalic acid (4), the same catalyst as mentioned above, may be present.

As the 3-substituted-2,4,5-trifluorobenzoic acid (6), 3-methoxy-2,4,5-trifluorobenzoic acid, 3-ethoxy-2,4,5trifluorobenzoic acid, 3-(n-propoxy)-2,4,5-trifluorobenzoic acid, 3-phenoxy-2,4,5-trifluorobenzoic acid or 3-(4'-methoxyphenoxy)-2,4,5-trifluorobenzoic acid may, for example, be mentioned. The 3-substituted-2,4,5-trifluorobenozic acid (6) is a compound useful as an intermediate for medicines and agricultural chemicals. The compound is particularly useful as a starting material for a quinolone-type bactericide, and a quinolone compound having a $R^3O$ group bonded at the 8-position of quinolone structure, can be synthesized in accordance with a conventional method.

The present invention will be described in further detail with reference to Examples. However, it should be understood that the present invention is by no means restricted by such specific Examples.

EXAMPLE 1

Into a 2 l glass reactor equipped with a reflux condenser and a stirrer, 500 g (1.74 mols) of tetrachlorophthalic anhydride, 441 g (2.10 mols) of phosphorus pentachloride and 100 g of phosphorus oxychloride were charged, and the mixture was heated to 135° C. without stirring. Then, it was stirred for 18 hours while maintaining the temperature at 140°±5° C. Then, phosphorus oxychloride was removed by distillation. Then, phosphorus oxychloride and phosphorus pentachloride were distilled off under reduced pressure. The temperature of the reactor was lowered to 120° C., and 200 g of toluene and 2 l of hexane were gradually added thereto, and the mixture was left to stand overnight. Crystals were collected by filtration and dried under reduced pressure to obtain 430.0 g of 3,3,4,5,6,7-hexachloro-1-[3H]-isobenzofuranone. The yield was 72.1%.

EXAMPLE 2

Into a 1l glass reactor equipped with a reflux condenser and a stirrer, 80 g (0.235 mol) of the 3,3,4,5,6,7-hexachloro-1-[3H]-isobenzofuranone prepared in Example 1, 109.0 g (1.88 mols) of spray dried potassium fluoride and 320 g of sulfolane were charged, and the mixture was reacted at 130°° C. for 5 hours with vigorous stirring. Then, the reaction solution was subjected to distillation to obtain 42.8 g of a mixture (1:1) of 3,4,5,6-tetrafluorophtaloyldifluoride and 3,3,4,5,6,7-hexafluoro-1-[3H]-isobenzofuranone. yield was 75.2%. From the mixture, 3,3,4,5,6,7-hexafluoro-1-[3H]-isobenzofuranone was separated by distillation, and the $^{19}$F–NMR spectrum and the boiling point were measured. $^{19}$F–NMR(CD$_3$COCD$_3$, CFCl$_3$)δ:–76.4(s,2F), –136.0(m,1F),–140.2(m,1F),–140.7(m,1F),–146.1(m,1F) bp. 47° C./7mmHg

EXAMPLE 3

Into a 500 ml glass reactor equipped with a reflux condenser and a stirrer, 100 g (0.413 mol) of the mixture (1:1) of the 3,4,5,6-tetrafluorophthaloyldifluoride and the 3,3,4,5,6,7-hexafluoro-1-[3H]-isobenzofuranone of Example 2, 43.8 g (0.413 mol) of sodium carbonate and 200 g of xylene were charged, and the mixture was reacted at 130° C. for 3 hours with vigorous stirring. Then, the inorganic substance was removed by filtration, and the residue was subjected to distillation to obtain 83.1 g of tetrafluorophthalic anhydride. The yield was 91.5%.

EXAMPLE 4

Into a 500 ml glass reactor equipped with a reflux condenser and a stirrer, a 100 g (0.413 mol) of a mixture (1:1) of the 3,4,5,6-tetrafluorophthaloyldifluoride and the 3,3,4,5,6,7-hexafluoro-1-[3H]-isobenzofuranone of Example 2, and 43.8 g (0.413 mol) of sodium carbonate were charged, and the mixture was reacted at 130° C. for 5 hours with vigorous stirring. Then, the reaction mixture was subjected to distillation to obtain 75.6 g of tetrafluorophthalic anhydride. The yield was 83.2%.

EXAMPLE 5

Into a 100 ml glass reactor equipped with a reflux condenser and a stirrer, 50 g (0.207 mol) of the mixture (1:1) of the 3,4,5,6-tetrafluorophthaloyldifluoride and the 3,3,4,5,6,7-hexafluoro-1-[3H]-isobenzofuranone of Example 2, and 17.4 g (0.207 mol) of sodiumhydrogen carbonate were charged, and the mixture was reacted at 130° C. for 5 hours with vigorous stirring. Then the reaction mixture was separated by distillation to obtain 33.0 g of tetrafluorophthalic anhydride. The yield was 72.5%.

EXAMPLE 6

Into a 500 ml glass reactor equipped with a reflux condenser and a stirrer, 100 g (0.413 mol) of the 3,4,5,6-tetrafluorophthaloyldifluoride separated by distillation from the mixture of Example 2, 43.8 g (0.413 mol) of sodium carbonate and 200 g of xylene were charged, and the mixture was reacted at 130° C. for 1.5 hours with vigorous stirring. Then, the inorganic substance was removed by filtration, and the residue was separated by distillation to obtain 84.9 g of tetrafluorophthalic anhydride. The yield was 93.4%.

EXAMPLE 7

Into a 500 ml glass reactor equipped with a reflux condenser and a stirrer, 100 g (0.413 mol) of the 3,3,4,5,6,7-hexafluoro-1-[3H]-isobenzofuranone separated by distillation from the mixture of Example 2, and 43.8 g (0.413 mol) of sodium carbonate were charged, and the mixture was reacted at 130° C. for 8 hours with vigorous stirring. Then, the reaction mixture was separated by distillation to obtain 79.5 g of tetrafluorophthalic anhydride. The yield was 87.5%.

EXAMPLE 8

Into a 200 ml glass reactor equipped with a reflux condenser and a stirrer, 50 g (0.207 mol) of the mixture (1:1) of the 3,4,5,6-tetrafluorophthaloyldifluoride and the 3,3,4,5,6,7-hexafluoro-1-[3H]-isobenzofuranone of Example 2, and 50 ml of acetic acid were charged, and the mixture was refluxed for 16 hours with vigorous stirring. Then, the reaction mixture was separated by distillation to obtain 29.3 g of tetrafluorophthalic anhydride. The yield was 64.3%.

EXAMPLE 9

Into a 200 ml glass reactor equipped with a reflux condenser and a stirrer, 50 g (0.207 mol) of the mixture (1:1) of the 3,4,5,6-tetrafluorophthaloyldifluoride and the 3,3,4,5,6,7-hexafluoro-1-[3H]-isobenzofuranone of Example 2, and 50 ml of trifluoroacetic acid were charged, and the mixture was refluxed for 72 hours with vigorous stirring. Then, the reaction mixture was separated by distillation to obtain 29.6 g of tetrafluorophthalic anhydride. The yield was 65%.

EXAMPLE 10

Into a 200 ml glass reactor equipped with a reflux condenser and a stirrer, 50 g (0.207 mol) of the mixture (1:1) of the 3,4,5,6-tetrafluorophthaloyldifluoride and the 3,3,4,5,6,7-hexafluoro-1-[3H]-isobenzofuranone of Example 2, and 79.0 g (0.414 mol) of 2,4-dichlorobenzoic acid were charged, and the mixture was reacted at 150° C. for 6 hours with vigorous stirring. Then, the reaction mixture was separated by distillation to obtain 28.5 g of tetrafluorophthalic anhydride. The yield was 62.5%.

EXAMPLE 11

Into a 300 ml glass reactor equipped with a reflux condenser and a stirrer, and 50 g (0.207 mol) of the mixture (1:1) of the 3,4,5,6-tetrafluorophthaloyldifluoride and the 3,3,4,5,6,7- hexafluoro-1-[3H]-isobenzofuranone, 59.3 g (0.31 mol) of 2,4-dichlorobenzoic acid and 100 ml of xylene were charged, and the mixture was reacted at 150° C. for 12 hours with vigorous stirring. Then, the reaction mixture was separated by distillation to obtain 32.8 g of tetrafluorophthalic anhydride. The yield was 72.05%.

EXAMPLE 12

Into a 300 ml glass reactor equipped with a reflux condenser and a stirrer, 100 g (0.413 mol) of the 3,4,5,6-tetrafluorophthaloyldifluoride separated by distillation from the mixture of Example 2, and 100 ml of acetic acid were charged, and the mixture was reacted at 130° C. for 1.5 hours with vigorous stirring. Then, the inorganic substance was removed by filtration, and the residue was separated by distillation to obtain 66.8 g of tetrafluorophthalic anhydride. The yield was 73.5%.

EXAMPLE 13

Into a 300 ml glass reactor equipped with a reflux condenser and a stirrer, 100 g (0.413 mol) of the 3,3,4,5,6,7-hexafluoro-1-[3H]-isobenzofuranone obtained in Example 2, and 100 ml of acetic acid were charged, and the mixture was reacted for 48 hours under reflux. Then, the reaction mixture was separated by distillation to obtain 79.5 g of tetrafluorophthalic anhydride. The yield was 87.5%.

EXAMPLE 14

Into a 100 ml glass reactor equipped with a reflux condenser and a stirrer, 20 g (0.091 mol) of the tetrafluorophthalic anhydride prepared in Example 3 and 40 ml of methanol were charged, and the mixture was stirred for 2 hours under reflux. After completion of the reaction, methanol was distilled off to obtain 22.5 g of 3,4,5,6-tetrafluorophthalic acid-monomethyl ester. The yield was 98.0%.

EXAMPLE 15

Into a 100 ml three necked flask, 20 g (0.079 mol) of the 3,4,5,6-tetrafluorophthalic acid-monomethyl ester prepared in Example 14, and 27.9 g (0.079 mol) of tri-n-octylamine were charged, and the mixture was heated and stirred at 140° C. for 4 hours. After completion of the reaction, the reaction mixture was separated by distillation to obtain 15.5 g of 2,3,4,5-tetrafluorobenzoic acid methyl ester. The yield was 94.2%.

EXAMPLE 16

Into a 100 ml three necked flask, 20 g (0.079 mol) of the 3,4,5,6-tetrafluorophthalic acid-monomethyl ester prepared in Example 14, and 2.8 g (0.0079 mol) of tri-n-octylamine were charged, and the mixture was heated and stirred at 140° C. for 24 hours. After completion of the reaction, the reaction mixture was separated by distillation to obtain 14.2 g of 2,3,4,5tetrafluorobenzoic acid methyl ester. The yield was 86.3%.

EXAMPLE 17

Into a 300 ml three necked flask, 20 g (0.096 mol) of the 2,3,4,5-tetrafluorobenzoic acid-methyl ester prepared in Example 15 and 40 g of 70 wt % sulfuric acid were charged, and the mixture was reacted for 10 hours at 140° C. with stirring. Then, 100 ml of water was added to the reaction solution, and the mixture was left to cool. Then, the mixture was extracted with hot toluene. Then, the solvent was distilled off to obtain 17.1 g of 2,3,4,5-tetrafluorobenzoic acid. The yield was 92%.

EXAMPLE 18

Into a 100 ml glass reactor equipped with a reflux condenser and a stirrer, 20 g (0.091 mol) of the tetrafluorophthalic anhydride prepared in Example 3 and 32.2 g (0.091 mol) of tri-n-octylamine were charged and 3.5 g (0.109 mol) of methanol was dropwise added thereto. Then, the mixture was reacted at 140° C. for 4 hours. After completion of the reaction, the reaction mixture was separated by distillation to obtain 17.5 g of 3,4,5,6-tetrafluorobenzoic acid methyl ester. The yield was 92.3%.

EXAMPLE 19

Into a 100 ml glass reactor equipped with a reflux condenser, a stirrer and a dropping funnel, 20 ml of a methanol solution of 10 g (0.0397 mol) of the 3,4,5,6-tetrafluorophthalic acid-monomethyl ester prepared in Example 14, was charged. Then, 44.9 g (0.0833 mol) of a 10% methanol solution of sodium methoxide was dropwise added thereto. The mixture was stirred for one hour under reflux. After completion of the reaction, the reaction mixture was neutralized with a 10% hydrochloric acid aqueous solution and extracted with ethyl acetate. Then, the solvent was distilled off to obtain 9.14 g of 4-methoxy-3,5,6-trifluorophthalic acid-1-methyl ester. (=5-methoxy-3,4,6-trifluorophthalic acid-2-methyl ester.) The yield was 87.2%.

EXAMPLE 20

Into a 100 ml glass reactor equipped with a reflux condenser, a stirrer and a dropping funnel, 20 ml of a methanol solution of 10 g (0.0397 mol) of the 3,4,5,6-tetrafluorophthalic acid-monomethyl ester prepared in Example 14 was charged, and then 4.6 g (0.083 mol) of potassium hydroxide was added thereto. The mixture was stirred for one hour under reflux. After completion of the reaction, the reaction mixture was neutralized with a 10% of hydrochloric acid aqueous solution and extracted with ethyl acetate. Then, the solvent was distilled off to obtain 8.2 g of 4-methoxy-3,5,6-trifluorophthalic acid-1-methyl ester. (=5-methoxy-3,4,6-trifluorophthalic acid-2-methyl ester.) The yield was 78.2%.

EXAMPLE 21

Into a 100 ml glass reactor equipped with a reflux condenser, a stirrer and a dropping funnel, 20 ml of a methanol solution of 10 g (0.0397 mol) of the 3,4,5,6-tetrafluorophtalic acid-monomethyl ester prepared in Example 14 was charged. Then, 8.21 g (0.060 mol) of potassium carbonate was added thereto. The mixture was stirred for 3 hours under reflux. After completion of the reaction, the reaction mixture was neutralized with a 10% hydrochloric acid aqueous solution and extracted with ethyl acetate. Then, the solvent was distilled off to obtain 8.7 g of 4-methoxy-3,5,6-trifluorophthalic acid-1-methyl ester. (=5-methoxy-3,4,6-trifluorophthalic acid-2-methyl ester.) The yield was 83.1%.

EXAMPLE 22

Into a 100 ml three necked flask, 10 g (0.0379 mol) of the 4-methoxy-3,5,6-trifluorophtahlic acid-1-methyl ester prepared in Example 21 and 20 g of a 10% sodium hydroxide aqueous solution were charged, and the mixture was stirred for 14 hours under reflux. After completion of the reaction, the reaction mixture was neutralized with a 10% of hydrochloric acid aqueous solution and extracted with ethyl acetate. Then, the solvent was distilled off to obtain 8.9 g of 4-methoxy-3,5,6trifluorophthalic acid. The yield was 94.0%.

EXAMPLE 23

Into a 100 ml three necked flask, 10 g (0.04 mol) of the 4-methoxy-3,5,6-trifluorophthalic acid prepared in Example 22 and 14.2 g (0.04 mol) of trioctylamine were charged, and the mixture was reacted at 140° C. for 4 hours with stirring. After completion of the reaction, 30 ml of a 20% sodium hydroxide aqueous solution was added thereto and stirred. The aqueous phase was separated and neutralized with a 10% hydrochloric acid aqueous solution and extracted with ethyl acetate. Then, the solvent was distilled off to obtain 7.17 g of 3-methoxy-2,4,5-triflourobenzoic acid. The yield was 87.0%

EXAMPLE 24

Into a 100 ml glass reactor equipped with a reflux condenser and a stirrer, 10 g (0.0397 mol) of the tetrafluorophthalic anhydride prepared in Example 3 and 20 ml of methanol were charged, and the mixture was stirred for 2 hours under reflux. After cooling, 42.8 g (0.079 mol) of a 10% methanol solution of sodium methoxide was dropwise added thereto. Then, under reflux, the mixture was stirred for one hour. Then, 15.9 g of a 10% sodium hydroxide aqueous solution was added thereto and the mixture was stirred for 12 hors under reflux. After cooling, 8 g of a 20% hydrochloric acid aqueous solution was added. Further, 21.1 g (0.0596 mol) of trioctylamine and 40 g of xylene were added thereto, and the mixture was stirred. The organic layer was separated and stirred at 140° C. for 2 hours. After completion of the reaction, 30 ml of a 20% sodium hydroxide aqueous solution was added thereto and stirred. The aqueous phase was separated and neutralized with a 10% hydrochloric acid aqueous solution and extracted with ethyl acetate. The solvent was distilled off to obtain 6.7 g of 3-methoxy-2,4,5-trifluorobenzoic acid. The yield was 81.5%.

According to the process of the present invention, tetrafluorophthalic anhydride can be obtained efficiently using a readily available compound as a starting material. Each reaction is easy and safe and provides good yield. Accordingly, the process is very advantageous from the industrial point of view.

Further, according to the process of the present invention, 2,3,4,5-tetraflourobenzocic acid and a 3-substituted-2,4,5-trifluorobenzoic acid can be obtained safely by using a readily available starting material without requiring dangerous reagent or operation. This process is an excellent process whereby the yield is good and the reaction conditions are mild. Further, the process comprises a small number of stages, and the reaction requires no special reagent or conditions, whereby the process is very advantageous when conducted on an industrial scale.

What is claimed is:

1. 3,3,4,5,6,7-Hexafluoro-1-[3H]-isobenzofuranone.

2. A process for producing 2,3,4,5-tetraflourobenzoic acid, which comprises reacting tetrafluorophthalic anhydride with a hydroxyl compound to obtain a 3,4,5,6-tetraflourophthalic acid-monoester, then decarboxylating it to obtain a 2,3,4,5-tetrafluorobenzoic acid ester, and further hydrolyzing it to obtain 2,3,4,5-tetrafluorobenzoic acid.

3. A process for producing a 2,3,4,5-tetrafluorobenzoic acid ester, which comprises reacting tetrafluorophthalic anhydride with an hydroxyl compound to obtain a 3,4,5,6-tetrafluorophthalic acid-monoester, and then decarboxylating it to obtain a 2,3,4,5-tetrafluorobenzoic acid ester.

4. A process for producing a 3-$R^3$O-substituted-2,4,5-trifluorobenzoic acid, which comprises reacting tetrafluorophthalic anhydride with a hydroxyl compound to obtain a 3,4,5,-tetrafluorophthalic acid-monoester, substituting the fluorine atom at the p-position to the ester group of said 3,4,5,6-tetrafluorophthalic acid-monoester by a $R^3$O group to obtain a 4-$R^3$O-substituted-3,5,6-trifluorophthalic acid-1-ester, then hydrolyzing it to obtain a 4-$R^3$O-substituted-3,5,6-trifluorophthalic acid, and further decarboxylating it to obtain a 3-$R^3$O-substituted-2,4,5-trifluorobenzoic acid, wherein $R^3$ is an alkyl, aryl or fluoroalkyl Group.

5. A process for producing a

4-$R^3$O-substituted-3,5,6-trifluorophthalic acid-1-ester, which comprises reacting tetrafluorophthalic anhydride with a hydroxyl compound to obtain a 3,4,5,6-tetrafluorophthalic acid-monoester, and substituting the fluorine atom at the p-position to the ester group of said 3,4,5,6-tetrafluorophthalic acid-monoester by a $R^3$O group to obtain a 4-$R^3$O-substituted-3,5,6-trifluorophthalic acid-1-ester, wherein $R^3$ is an alkyl, aryl or fluoroalkyl group.

6. The process according to any one of claims 4 to 5, wherein the 3,4,5,6-tetrafluorophthalic acid-monoester is a 3,4,5,6-tetrafluorophtalic acid-monoalkyl ester, a 3,4,5,6-tetrafluorophthalic acid-mono(fluoroalkyl)ester, or a 3,4,5,6-tetrafluorophthalic acid-mono(aryl)ester.

7. The process according to claim 4 or 5, wherein the substitution of the fluorine atom at the p-position to the ester group of the 3,4,5,6-tetrafluorophthalic acid-monoester by a $R^3$O group is conducted in the presence of a metal alkoxide, or a hydroxyl compound and inorganic base.

8. The process according to claim 4, wherein the 3-substituted-2,4,5-trifluorobenzoic acid is a 3-alkoxy-2,4,5-trifluorobenzoic acid, a 3-fluoroalkoxy-2,4,5-trifluorobenzoic acid, or a 3-aryloxy-2,4,5-trifluorobenzoic acid.

* * * * *